United States Patent [19]

Farrar et al.

[11] Patent Number: 5,798,093
[45] Date of Patent: *Aug. 25, 1998

[54] SPRAY FORMULATIONS OF ANTIHYPERALGESIC OPIATES AND METHOD OF TREATING TOPICAL HYPERALGESIC CONDITIONS AND PRURITUS THEREWITH

[75] Inventors: John J. Farrar, Chester Springs; An-Chih Chang, Bensalem; Alan L. Maycock, Malvern; Imre Balogh, Perkasie, all of Pa.

[73] Assignee: Adolor Corporation, Malvern, Pa.

[*] Notice: The term of this patent shall not extend beyond the expiration date of Pat. No. 5,667,773.

[21] Appl. No.: 892,389

[22] Filed: Jul. 14, 1997

Related U.S. Application Data

[63] Continuation-in-part of Ser. No. 818,559, Mar. 14, 1997.
[51] Int. Cl.$^6$ .................. A61L 9/04; A61K 31/74
[52] U.S. Cl. .................. 424/45; 424/78.05; 424/47
[58] Field of Search .................. 424/45, 78.05

[56] References Cited

U.S. PATENT DOCUMENTS

| | | | |
|---|---|---|---|
| 3,714,159 | 1/1973 | Jannsen et al. | 260/247.1 |
| 3,730,960 | 5/1973 | Watchung et al. | 252/106 |
| 3,884,916 | 5/1975 | Jannsen et al. | 260/247.1 |
| 5,035,883 | 7/1991 | Witkin | 422/29 |
| 5,516,808 | 5/1996 | Sawaya | 514/781 |
| 5,667,773 | 9/1997 | Farrar et al. | 424/28.05 |

OTHER PUBLICATIONS

McMahon et al., TINS, vol. 15, No. 12 (1992).

Bernstein et al., Journal of Investigative Dermatology, 78: 82–83 (1982).

Ballantyne et al., Pain, 33: 149–160 (1988).

J. D. Bernhard, J. Am. Acad. Derm. 24: 309 (1991).

IASP Newsletter, Sep./Oct. 1996.

Thomas et al., Brain Research, 695: 267–270 (1995).

*Primary Examiner*—Thurman K. Page
*Assistant Examiner*—Kathryne E. Shelborne
*Attorney, Agent, or Firm*—Imre Balogh

[57] ABSTRACT

Spray formulations of anti-pruritic opiates having a peripheral selectivity of 251 to 1,280 in a solvent mixture of up to 15% w/w alcohol selected from the group consisting of ethyl, propyl and isopropyl alcohol and water greater than or equal to 85% w/w water.

2 Claims, No Drawings

SPRAY FORMULATIONS OF ANTIHYPERALGESIC OPIATES AND METHOD OF TREATING TOPICAL HYPERALGESIC CONDITIONS AND PRURITUS THEREWITH

This application is a continuation-in-part of application Ser. No. 08/818,559, filed on Mar. 14, 1997.

BACKGROUND OF THE INVENTION

1. Field of the Invention

This invention relates to spray formulations of antihyperalgesic opiates having substantially no effects on the central nervous system and method of topically treating hyperalgesic conditions. More particularly, the invention relates to anti-hyperalgesic opiates in non-sting spray formulations for the treatment of topical hyperalgesic conditions associated with injuries.

The present invention also relates to compositions and methods for the prevention and/or treatment of itch, also known as pruritus, which has many causes. The compositions which are formulated for topical spray administration contain antihyperalgesic opiates that are substantially devoid of central nervous system effects and, thus, have very little, if any, potential for producing side effects associated with centrally acting antihyperalgesic opiates.

2. Reported Developments

A. Antihyperalgesic Opiates

Pain is the effect of noxious stimuli on nerve endings of a subject which results in the transmission of impulses to the cerebrum. This sensation informs the subject of actual or impending tissue damage and elicits a defensive response. The degree of response substantially correlates with the degree of noxious stimuli in order to speedily avoid further tissue damage and to re-establish normal pre-injury conditions in the subject. The sensation of pain, however, does not end with the stoppage of the noxious stimuli but continues to persist during the inflammation stage of the injury. In turn, the continuation of pain perception causes discomfort to, and deleteriously affects the well-being of, the subject. It is, therefore, important to reduce and/or eliminate pain perception of a subject subsequent to injuries.

The reduction/elimination of pain perception can be affected by the central nervous system (hereinafter sometimes referred to as CNS)-mediated analgesia which leads to an overall inhibition of the pain transmission. CNS-mediated analgesia can be effected by systemically administered opiates which, by interaction with specific receptors in the brain and spinal cord, are able to block pain transmission. Systemic opiates, such as morphine, which have been used for many years to control post injury pain, have side effects because their actions within the brain include sedation, depression of respiration, constipation, nausea and development of addiction and dependence. When peripherally applied, opiates have a short duration of action and still possess the undesirable side effects.

Certain opiates, such as loperamide [i.e., 4-(p-chlorophenyl)-4-hydroxy-N-N-dimethyl-α,α-diphenyl-1-piperidinebutyramide hydrochloride] and its analogs were reported to be devoid of CNS effects, which is believed to be due to the failure of the opiates to cross the blood brain barrier. Loperamide HCl has been used for a long time in antidiarrheal formulations and has been completely free of the undesirable CNS effects. It is desirable to use such opiates to inhibit/eliminate post-injury pain without concomitant CNS effects.

Spray formulations for topical application for cleansing the injured site are known and have been used by the prior art. Some of these formulations, known as first aid sprays and antiseptics are applied to the site of the injury subsequent to flushing the site with water to remove foreign matter originating from the source of injury or the environment. The substance contained in these sprays kills or prevents the growth of microorganisms. A number of antiseptic drugs are oxidizing agents which include: peroxides, such as hydrogen peroxide; permanganates, such as potassium permanganates, benzene derivatives and phenols. Specific examples of antiseptic agents include chlorhexidine, calcium iodate, iodine, chloroxylenol, hexachlorophene, boric acid and cupric sulfate.

Other pharmaceutical agents used to prevent or combat topical infection and to accelerate the healing process include:

Antibacterial agents, such as Streptomycin, Rifamycin, Ampicillin, Penicillin O, Penicillin V, Bacitracin, Doxycycline, Methacycline, Minocycline, Tetracycline, Acetyl Sulfisoxazole, Succinylsulfathiazole, Sulfaloxic Acid, Sulfapyrazine, and Acetosulfone;

Antifungal agents, such as Dermostatin, Fungichromin, Clotrimazole, Econazole, Potassium Iodide, Propionic Acid, Ketoconazole, Cicloprox Olamine, Tolnaftate and Naftifine;

Anti-inflammatory agents, such as Diclofenac, Tolmetin, Ibuprofen, Protizinic Acid, Glycol Salicylate and Sulfasalazine.

Antibiotics, such as Clindamycin, Erythromycin, Tetracycline, Mupirocin, Bacitracin and Neomycin;

Antiseptic agents such as Chlorhexidine, Calcium Iodate, Iodine, Chloroxylenol, Hexachlorophene, Boric Acid, and Cupric Sulfate; and Antiviral agents, such as Acyclovir, Trifluridine and Zidovudine.

These and other agents used on the site of injury tend to produce stinging, pricking, burning and pain so that their utility to prevent or combat infection and to promote healing is limited to those individuals who are willing to accept these undesirable sensations. This drawback of first aid products is accentuated in the treatment of children having wounds, abrasions and burns who are reluctant to suffer the stinging effect of the products.

Peripheral antihyperalgesic compounds which inhibit sensation of pain without CNS side effects would provide a solution to the problem. It has now been discovered that such peripheral antihyperalgesic compounds can render the spray formulations acceptable for delivering agents customarily used in the treatment of topical wound abrasions, burns and the like to prevent infection and accelerate wound healing.

In the course of our investigation, however, we have encountered another problem in delivering the spray formulation to the site of treatment. The peripheral antihyperalgesic compounds are essentially insoluble/sparingly soluble in water. Their solubility in water is about 0.002% w/w to 5% w/w. To provide for the inhibition of pain, very large amounts of the peripheral antihyperalgesic compounds were required. The use of such large amounts, on the other hand, caused clogging of the spray nozzle and deposition of the compounds on the wall of the container from which the aqueous solution of the compounds were dispensed.

While the peripheral antihyperalgesic compounds are soluble in organic solvents, the use of such solvents is very limited for treating topical injuries. The organic solvents having oily consistency tend to hold the active compounds and do not allow quick and sufficient release to the site of injury to be treated.

Other organic solvents without oily consistency, such as methanol, have deleterious effects on open wounds through which they can enter the blood circulation system.

Accordingly, ethanol, propanol and isopropanol were selected as carriers in which the active compounds are soluble and which can be used on open wounds without deleterious side effects. However, these vehicles alone or in an aqueous mixture in which they constituted a substantial amount resulted in stinging and burning sensations rendering the vehicle unsuitable for the delivery of the active agent. Although, during the period of spraying a pleasant cooling effect was observed, the subsequent absorption of the vehicle increased the pain already present at the site of injury.

With extensive experimentation we have now discovered that an effective antihyperalgesic non-sting spray formulation can be provided by incorporating an antihyperalgesic opiate having a peripheral selectivity of from about 251 to about 1,280 in an aqueous alcohol mixture of up to about 15% w/w ethyl-alcohol, propyl alcohol or isopropyl alcohol.

B. Antihyperalgesic Opiates as Anti-Pruritic Agents

The prior art has investigated the physiology and treatment of pruritus as illustrated hereunder.

Itch is a well known sensory state associated with the desire to scratch. As with pain, itch can be produced by a variety of chemical, mechanical, thermal or electrical stimuli. In addition to the difference in the sensory quality of itch and pain, they also differ in that (1) itch, unlike pain, can only be evoked from the superficial layers of skin, mucosa, and conjunctiva, and (2) itch and pain usually do not occur simultaneously from the same skin region; in fact, mildly painful stimuli, such as scratching, are effective in eliminating itch. In addition, the application of histamine to skin produces itch but not pain. Itch and pain are further dissociated pharmacologically: itch appears to be insensitive to opiate and non-steroidal anti-inflammatory drug (NSAID) treatment, both of which are effective in treating pain.

Although itch and pain are of a class in that both are modalities of nociception transmitted by small unmyelinated C fibers, evidence that itch is not just a variety of low-threshold pain is overwhelming. Itch leads to the reflex or urge to scratch; pain leads to withdrawal. Itch occurs only in the skin; pain arises from deeper structures as well. Heat may stop pain but usually increases pain. Removal of the epidermis eliminates itch but causes pain. Analgesics, particularly opiods, relieve pain but often cause itch (see, for example *J. Am. Acad. Derm.* 24: 309–310, 1991). There can be no doubt that itching is of eminent clinical importance; many systemic and skin diseases are accompanied by persistent or recurrent itch attacks. Current knowledge suggests that itch has several features in common with pain but exhibits intriguing differences as well (see, for example, W. Magerl, *IASP Newsletter*, pp. 4–7, Sept./Oct. 1996).

McMahon et al (*TINS*, Vol. 15, No. 12, pp. 497–501, 1992) provides a description of stimuli (Table a) and a comparison of the established features of itch and pain (Table b):

TABLE a

Stimuli that can elecit or augment itch

Physical

Mechanical. Light touch, pressure, suction.
Thermal. Warming.
Electrical. Focal transcutaneous repetitive stimulation, transcutaneous constant current stimulation, intraneural microstimulation.

Chemical

Non-specific irritants. Acids, alkalis.
Inflammatory mediators. Histamine, kallikrein, bradykinin, prostaglandins.
Histamine-releasing substances. Compound 48/80, protamine, C3a.
Peptidases. Mucunain, papain, trypsin, mast cell chymase.
Neuropeptides. Substance P, vasoactive intestinal polypeptide, neurotensin, secretin.
Opiods. Morphine, β-endorphin, enkephalin analogues.

TABLE b

Comparison of the established features of itch and pain

|  | ITCH | PAIN |
|---|---|---|
| Psychophysiology | | |
| Tissue | Skin. Mucous membranes | Most tissues |
| Stimulus | See Table a | Many stimuli |
| Intraneural microstimulation | Occasionally | Yes |
| Secondary sensations | Allokinesis (itchy skin) | Hyperalgesia |
| Psychogenic modification | Pronounced | Present |
| Counterstimuli | Scratching, pain, cooling | Tactile stimuli, cooling |
| Neurophysiology | | |
| Primary afferent neurons | C- and Aδ-fibres | C- and Aδ-fibres |
| Flare size | Large | Small |
| Spinal pathway | Anterolateral funiculus | Anterolateral funiculus |
| Protective reflexes | Scratching, sneezing | Flexion, guarding |
| Autonomic reflexes | Yes | Yes |
| Pharmacology | | |
| Capsaicin sensitivity | Yes | Chemogenic pain; yes |
| NSAID sensitivity | Probably not | Yes |
| Morphine sensitivity | No | Yes |

Abbreviation: NSAID, non-steroidal anti-inflammatory drugs.

Experimental focal itch stimuli are surrounded by a halo of seemingly unaffected tissue where light tactile stimuli are capable of eliciting itch-like sensations. The term itchy skin or allokinesis has been coined for these secondary, sensations that are reminiscent of the features of secondary hyperalgesia evolving around a painful focus. A crucial observation is that itch and pain usually do not coexist in the same skin region and a mild noxious stimulus such as scratching is in fact the singly most effective way to abolish itch. This abolition of itch can be prolonged producing an 'antipruritic state'. Although mild scratch is often not painful, microneurographic recordings from humans have directly determined that such stimuli are among the most effective ways to excite cutaneous unmyelinated nociceptive afferents. (See, for example:

Shelly, W. B. and Arthur, R. P. (1957) *Arch. Dermatol.* 76, 296–323;
Simone, D. A. et al. (1987) *Somatosens. Res.* 5, 81–92;
Graham, D. T., Goodell, H. and Wolff, H. G. (1951) *J. Clin. Invest.* 30, 37–49;
Simone, D. A., Alreja, M. and LaMotte, R. H. (1991) *Somatosens, Mot. Res.* 8, 271–279;

Torebjork, E (1985) *Philos. Trans. R. Soc. London Ser.* B 308, 227–234; and

Vallbo, A. B., Hagbarth, K. E., Torebjork, H. E. and Wallin, B. G. (1979) *Physiol. Rev.* 59, 919–957).

Physiologically, there is evidence that substance P released from nociceptor terminals can cause the release of histamine from mast cells. Activation of mast cells, with release of the pruritogen histamine, occurs in immediate type hypersensitivity diseases, such as anaphylactic reactions and urticaria. Urticarial eruptions are distinctly pruritic and can involve any portion of the body, and have a variety of causes beyond hypersensitivity, including physical stimuli such as cold, solar radiation, exercise and mechanical irritation. Other causes of pruritus include: chiggers, the larval form of which secretes substance that creates a red papule that itches intensely; secondary hyperparathyroidism associated with chronic renal failure; cutaneous larva migrans, caused by burrowing larvae of animal hookworms; dermal myiasis, caused by maggots of the horse botfly, which can afflict horseback riders; onchocerciasis ("river blindness") caused by filarial nematodes; pediculosis, caused by lice infestations; enterobiasis (pinworm) infestations, which afflict about 40 million Americans, particularly school children; schistosome dermatitis (swimmer's itch); poison ivy; excema, psoriasis; and asteatotic eczema ("winter itch"). The role of histamine or other endogenous pruritogens in mediating itch associated with these and other pruritic conditions, such as atopic dermatitis, its not yet well established. For atopic dermatitis, in particular, it appears that itch is not inhibited by antihistamines, but by cyclosporin A, a drug which inhibits the production of cytokines which have been proposed as potential pruritogens.

Current therapies for the treatment of itch include a variety of topical and systemic agents, such as steroids, antihistamines, and some psychotherapeutic tricyclic compounds, such as doxepin hydrochloride. Many such agents are listed in *PDR Generics* (see Second Edition, 1996, p. cv for a listing of said agents). The limitations of these agents are well known to medical practitioners, and are summarized in the "Warnings" and "Precautions" sections for the individual agents listed in *PDR Generics*. In particular, the lack of complete efficacy of antihistamines is well known, but antihistamines are frequently used in dermatology to treat pruritus due to urticaria, atopic dermatitis, contact dermatitis, psoriasis, and a variety of other conditions. Although sedation has been a frequent side effect of conventional systemically administered antihistamines, a new generation of antihistamines has been developed that are nonsedating, apparently due to their inability to cross the blood-brain barrier.

Intravenous administration of opiate analgesics, such as morphine and hydromorphone has been associated with pruritus, urticaria, other skin rashes, and wheat and flare over the vein being injected. These itch and itch-related reactions are believed to be due to a histamine-releasing property of these opiates, via mast cell degranulation. These opiates are thought to act upon the mu subtype of opiate receptor, but the possibility of interactions at the other principal opiate receptor subtypes (delta and kappa) cannot be excluded since these and other pruritogenic analgesics are not pure mu agonists. The cellular loci of the receptor type(s) mediating the itching effect is not known, although the mast cell is a possible candidate since opiates cause histamine release from these cells. However, some investigators have suggested that the frequent inability of antihistamines to block morphine-induced itching suggests a non-histaminergic mediation of opiate-induced itching—mechanism which could involve central opiate receptors. Although i.v. morphine only occasionally results in generalized itching (in about 1% of patients), pruritus is more prevalent in opiate analgesia with epidural (8.5%) or intraspinal (45.8%) administration. (See, for example: Bernstein et al., "Antipruritic Effect of an Opiate Antagonist, Naloxone Hydrochloride", *The Journal of Investigative Dermatology*, 78:82–83, 1982; and Ballantyne et al., "Itching after epidural and spinal opiates", Pain, 33: 149–160, 1988.)

To date, treatment with opiates has not only proven useless in the treatment of itch, but appears to exacerbate itch in man. The consistent findings from human studies indicate that whether by central or peripheral mechanisms, opiates appear to promote rather than prevent itching, and that opiate antagonists have antipuritic activity.

Human clinical studies have generally shown that opiates cause itching and there is evidence that these effects can be reproduced in animal models, where itching sensations per se cannot be reported, but scratching behavior can be observed. (See, for example: Thomas et al., "Microinjection of morphine into the rat medullary dorsal horn produces a dose-dependent increase in facial-scratching", *Brain Research*, 695: 267–270, 1996; Thomas et al., "Effects of central administration of opioids on facial scratching in monkeys", *Brain Res.*, 585: 315–317, 1992; and Thomas et al., "The medullary dorsal horn: A site of action of opioids in producing facial scratching in monkeys", *Anesthesiology*, 79: 548–554, 1993).

We have now surprisingly discovered that certain opiates, which are substantially devoid of central nervous system effects, in topical spray formulations possess anti-pruritic activity in addition to anti-hyperalgesic activity.

SUMMARY OF THE INVENTION

The present invention provides topical spray formulations and methods of using the formulations as anti-hyperalgesics.

The present invention further provides topical spray formulations for the prevention and treatment of pruritus.

The topical anti-hyperalgesic formulation comprises:

(A) a peripheral antihyperalgesic compound of the formula (I)

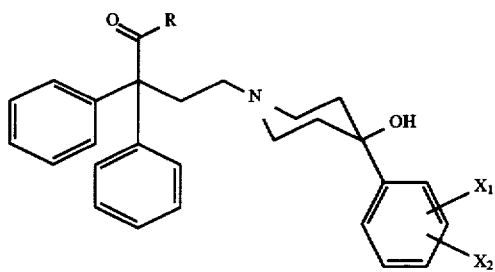

wherein

R is $N(CH_3)_2$, $N(CH_2CH_3)_2$, $N(CH_3)C_2H_5$, $N(CH_2)_4$, $N(CH_2)_5$ or $N(CH_2CH_2)_2O$; and $X_1$ and $X_2$ are independently H, Cl, Br, F or $CF_3$ and wherein said antihyperalgesic compound has a peripheral selectivity of from about 251 to about 1,280;

(B) a solvent mixture for the compound of formula I comprising: a) up to about 15% w/w of an alcohol selected from the group consisting of ethyl alcohol, propyl alcohol and isopropyl alcohol or mixtures thereof; and b) greater than or equal to 85% w/w water; and C) one or more additional active ingredients selected from the group consisting of antibacterials, antivirals, antifungals, anti-inflammatories and anesthetics or mixtures thereof.

The topical anti-pruritic formulation comprises the same compound and solvent mixture as the antihyperalgesic formulation:

(A) a peripheral anti-pruritic compound of the formula (II)

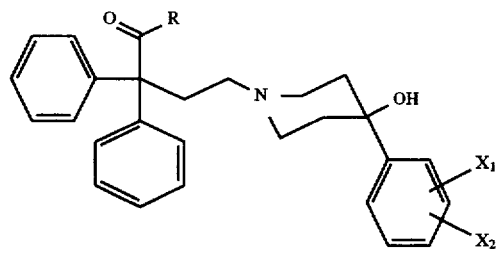

wherein

R is $N(CH_3)_2$, $N(CH_2CH_3)_2$, $N(CH_3)C_2H_5$, $N(CH_2)_4$, $N(CH_2)_5$ or $N(CH_2CH_2)_2O$; and $X_1$ and $X_2$ are independently H, Cl, Br, F or $CF_3$ and wherein said anti-pruritic compound has a peripheral selectivity of from about 251 to about 1,280; and (B) a solvent mixture for the compound of formula II comprising: a) up to about 15% w/w of an alcohol selected from the group consisting of ethyl alcohol, propyl alcohol and isopropyl alcohol or mixtures thereof; and b) greater than or equal to 85% w/w water.

The spray formulations of formulae I and II may be contained in a propellant mixture or they may be dispensed from a pump-action container or the like.

Preferred antihyperalgesic compounds used in the present invention are:

(1) 1-[4-(4-Hydroxy-4-phenyl-1-piperidino)-2,2-diphenylbutyryl]piperidine [R=$N(CH_2)_5$; $X_1$=H; $X_2$=H]

(2) 4-(p-Chlorophenyl)-4-hydroxy-N-ethyl-N-methyl-α,α-diphenyl-1-piperidinebutyramide [R=NMe Et; $X_1$=4-Cl; $X_2$=H]

(3) 4-(p-Bromophenyl)-4-hydroxy-N,N-dimethyl-α,α-diphenyl-1-piperidinebutyramide [R=$NMe_2$; $X_1$=4-Br; $X_2$=H]

(4) 1-{4-[(3,4-Dichlorophenyl)-4-hydroxy-1-piperidino-2,2-diphenylbutyryl}pyrrolidine [R=$N(CH_2)_4$; $X_1$=3-Cl; $X_2$=4-Cl]

(5) 1-{4-[(4-Chlorophenyl)-4-hydroxy-1-piperidino]-2,2-diphenylbutyryl}pyrrolidine [R=$N(CH_2)_4$; $X_1$=4-Cl; $X_2$=H]

(6) 4-(p-Chlorophenyl)-4-hydroxy-N,N-dimethyl-α,α-diphenyl-1-piperidinebutyramide [R=$NMe_2$; $X_1$=4-Cl; $X_2$=H]

(7) 4-(p-Fluorophenyl)-4-hydroxy-N,N-dimethyl-α,α-diphenyl-1-piperidinebutyramide [R=$NMe_2$; $X_1$=4-F; $X_2$=H]

(8) 4-(4-Chloro-3-trifluoromethyl-phenyl)-4-hydroxy-N,N-dimethyl-α,α-diphenyl-1-piperidinebutyramide [R=$NMe_2$; $X_1$=4-Cl; $X_2$=3-$CF_3$]

(9) 1-[4-(4-Hydroxy-4-phenyl-1-piperidino)-2,2-diphenylbutyryl]pyrrolidine and [R=$N(CH_2)_4$; $X_1$=H; $X_2$=H]

(10) 1-{4-[4-Hydroxy-4-(3-trifluoromethylphenyl)-1-piperidino]-2,2-diphenylbutyryl}morpholine [R=$N(CH_2CH_2)_2O$; $X_1$=3-$CF_3$; $X_2$=4-H]

The peripheral selectivity of these compounds are shown in Table I.

TABLE I

| Compound | Peripheral Selectivity ($ED_{50tw}/ED_{50}$ Castor Oil) |
|---|---|
| 1 | >1,280 |
| 2 | ≧1,231 |
| 3 | 800 |
| 4 | >640 |
| 5 | 593 |
| 6 | 533 |
| 7 | 500 |
| 8 | 467 |
| 9 | 437 |
| 10 | >251 |

Peripheral selectivity is defined by the ratio of the $ED_{50}$ in the tail-withdrawal assay over the $ED_{50}$ in the anti-diarrheal assay. The assay results for the above listed compounds were obtained by the test methods described hereunder.

Measure of Centrally-Mediated Opiod Analgesia by the Tail-Withdrawal Assay (Janssen, P. A. J.; Niemegeers, C. J. E.; Dony, J. G. H., The Inhibitory effect of Fentanyl and other morphine-like analgesics on the warm water induced tail withdrawal reflex in rats. Arzneimittel-Forschung 1963, 13, 502–507.)

Young female Wistar rats (170–210 g body weight) are used only once. They are fed and watered ad libitum in their living quarters until 7:00 AM of the day of the experiment, when they are brought to the laboratory to be put into individual restraining cages on hour later until the end of the experiment. The lower 5 cm portion of the tail is marked. Around 8:30 AM the "normal" reaction time of each rat is determined by immersing the lower 5 cm portion of the tail in a cup freshly filled with water from a large constant temperature (55° C.) bath until the typical tail withdrawal response is observed. The cut off time is 15 seconds. The reaction time is measured in 0.5 second units with a stopwatch. After each determination the tail is carefully dried. Around 9:00 AM each rat is given saline (control rats) or an aqueous solution (or suspension) of the substance to be investigated by the oral route of administration. Periodically thereafter (i.e., ¼, ½, 1, 2, 3, 4, 5 and 6 hours after dosage) the reaction time is again measured by trained technicians unaware of the nature of the compounds. Results of these studies are expressed as $ED_{50}$ concentration values (mg/kg), calculated as the dose producing a tail withdrawal latency equal to half the difference between the maximum latency (≦15 seconds) and the baseline latency (6 to 8 seconds).

Castor Oil Test in Rats [see, e.g. Niemegeers et al (1972) Arzneim Forsch. 22:516–518; U.S. Pat. No. 4,867,979; U.S. Pat. No. 4,990,521; U.S. Pat. No. 4,824,853]

Young female Wistar rats (230–250 g body weight) are fasted overnight and in the morning each animal is treated orally with a dose level of the compound to be tested. One hour thereafter, the animal received 1 ml of castor oil orally. Each animal is kept in an individual cage. At different selected time intervals (e.g. 1, 2, 3, 4, 6 and 8 hrs) after the castor oil treatment, the presence or absence of diarrhea is noted. In more than 95% of 500 control animals, severe diarrhea is observed 1 hour after treatment with castor oil. Using this all-or-none criterion, a significant positive effect occurs with the tested compound if no diarrhea is observed 1 hour after the castor oil treatment. A minimum of 5 dose levels are use per drug, each dose level being given to 10 rats on ten different days. The $ED_{50}$ value is determined as that dose in mg/kg body weight at which no diarrhea is present in 50% of the tested animals.

The solvent mixture for the compounds of formula I and formula II is preferably of from about 1% w/w to 15% w/w, more preferably of from 2 to 10% w/w, and most preferably of from 5 to 8% w/w of an alcohol selected from the group consisting of ethanol, propanol or isopropanol and of from about 99% w/w to about 85% w/w water.

DETAILED DESCRIPTION OF THE INVENTION

The Anti-Hyperalgesic/Anti-Pruritic Compounds

The compounds for use in the compositions and methods herein possess peripheral anti-hyperalgesic and anti-pruritic activity and substantially no CNS activities because they do not cross the blood brain barrier. The failure to cross the blood brain barrier precludes the occurrence of the CNS systemic side effects, so that there is no potential for abuse. The compounds for use in the methods and compositions provided herein include compounds that by virtue of their interaction, either directly or indirectly, with peripheral opioid receptors ameliorate the peripheral hyperalgesic state, but do not exhibit systemic CNS-mediated analgesic activity or CNS side effects, including heaviness of the limbs, flush or pale complexion, clogged nasal and sinus passages, dizziness, depression, respiratory depression, sedation and constipation. These compounds include antidiarrheals that act as antidiarrheals via interaction, with $\mu$, $\delta$, or $\kappa$ receptors, and opiate agonists, such as metkephamide and related enkephalin analogs. The compounds of the present invention have been reported in prior art patents U.S. Pat. Nos. 3,714,159 and 3,884,916 which are incorporated herein by reference.

Representative examples are included according to said patents to illustrate the preparation of some compounds used in the present invention.

EXAMPLE 1

1-[4-(4-Hydroxy-4-phenylpiperidino)-2,2-diphenylbutyryl]piperidine hydrochloride A mixture of 13.5 parts of 1-(tetrahydro-3,3-diphenyl-2-furylidene) piperidinium bromide, 5.3 parts of 4-phenyl-4-piperidinol, 8 parts of sodium carbonate, 0.2 parts of potassium iodide and 200 parts of 4-methyl-2-pentanone is stirred and refluxed for 3 hours with water-separator. The reaction mixture is cooled and 200 parts of water is added. The organic layer is separated, dried and evaporated. The solid residue is crystallized from 120 parts of 4-methyl-2-pentanone (activated charcoal), yielding 7.8 parts of the crude free base of 1-[4-(4-hydroxy-4-phenyl-piperidino)-2,2diphenylbutyryl]piperidine hydrochloride. It is dissolved in 4-methyl-2-pentanone and this solution is acidified with an excess of 2-propanol previously saturated with gaseous hydrogen chloride. The precipitated salt is filtered off and dried, yielding 1-[4-(4-hydoxy-4-phenylpiperidino)-2,2-diphenylbutyryl|piperidine hydrochloride; m.p. 240.3° C.

EXAMPLE 2

4-(p-Chlorophenyl)-4-hydroxy-N,N-dimethyl-$\alpha$,$\alpha$-diphenylpiperidine-1-butyramide hydrochloride A mixture of 6.33 parts of 4-(p-chlorophenyl)-4piperidinol, 8 parts sodium carbonate, 0.2 parts of potassium iodide and 240 parts of 4-methyl-2-pentanone is distilled azeotropically. Then there are added 12.12 parts of dimethyl (tetrahydro-3,3-diphenyl-2-furylidene)ammonium bromide and the whole is stirred and refluxed for about 15 hours. The reaction mixture filtered hot and the filtrate is evaporated. The oily residue is dissolved in 2-propanol and to this solution is added an excess of 2-propanol previously saturated with gaseous hydrogen chloride. The whole is evaporated and the oily residue is warmed in diluted hydrochloric acid solution. Upon the addition of toluene, the salt is precipitated. It is filtered off, boiled in acetone, and filtered off again after cooling, yielding 4-(p-Chlorophenyl)-4-hydroxy-N,N-dimethyl-$\alpha$,$\alpha$-diphenyl-piperidine-1-butyramide hydrochloride; m.p. 221.1° C.

EXAMPLE 3

1-[4-(4-Hydroxy-4-phenylpiperidino)-2,2-diphenylbutyryl]pyrrolidine

A mixture of 13 parts of 1-(tetrahydro-3,3-diphenyl-2-furylidene) pyrrolidinium bromide, 5.3 parts of 4-phenyl-4-piperidinol, 8 parts of sodium carbonate, 0.2 parts of potassium iodide and 200 parts of 4-methyl-2-pentanone is stirred and refluxed for 5 hours with water separator. The reaction mixture is cooled and water is added. The organic layer s separated, washed with diluted sodium hydroxide solution, dried, filtered, and while stirring the filtrate, the product is crystallized. It is filtered off and dried, yielding 1-[4-(4-hydroxy-4-phenylpiperidino)-2,2-diphenylbutyryl| pyrrolidine; m.p. 187.5° C.

EXAMPLE 4

4-(4-Chloro-3-trifluoromethylphenyl)-4-hydroxy-N,N-dimethyl-$\alpha$,$\alpha$-diphenylpiperidine-1-butyramide hydrochloride A mixture of 12.1 parts of dimethyl (tetrahydro-3,3-diphenyl-2-furylidene) ammonium bromide, 8.4 parts of 4-(4-chloro-3-trifluoromethylphenyl)-4-piperidinol, 8 parts of sodium carbonate, 0.4 parts of potassium iodide and 200 parts of 4-methyl-2-pentanone is stirred and refluxed for 3 hours with water separator. The reaction mixture is cooled and water is added. The organic layer is separated, washed with diluted sodium hydroxide solution, dried and concentrated to a volume of about 200 parts. The concentrate is acidified with an excess of 2-propanol previously saturated with gaseous hydrogen chloride. Upon stirring, the salt is crystallized. It is filtered off and dried, yielding 4-(4-chloro-3-trifluoromethylphenyl)-4-hydroxy-N,N-dimethyl-$\alpha$,$\alpha$-diphenylpiperidine-1 -butyramide hydrochloride; m.p. 215.3° C.

EXAMPLE 5

4-(p-Bromophenyl)-4-hydroxy-N,N-dimethyl-$\alpha$,$\alpha$-diphenylpiperidine-1-butyramide hydrate A mixture of 12.1 parts of dimethyl (tetrahydro-3,3-diphenyl-2-furylidene) ammonium bromide, 8.8 parts of 4-(p-bromophenyl)-4-piperidinol hydrochloride, 10.6 parts of sodium carbonate, 0.5 parts of potassium iodide and 200 parts of 4-methyl-2-pentanone is stirred and refluxed for 14 hours with water separator. The reaction mixture is cooled and water (200 parts) is added. The organic layer is separated, washed with diluted sodium hydroxide solution, dried, filtered, and while stirring the filtrate, the product is crystallized. It is filtered off and recrystallized from 80 parts of 4-methyl-2-pentanone (activated charcoal), yielding 4-(p-bromophenyl)-4-hydroxy-N,N-dimethyl-$\alpha$,$\alpha$-diphenylpiperidine-1-butyramide hydrate; m.p. 123.7° C.

The anti-hyperalgesic/anti-pruritic compounds are dissolved in the alcohol-water mixture and can be dispensed as anti-hyperalgesic/anti-pruritic spray from containers having a pump action or from aerosol containers which are charged with propellants. The spray on the site of injury will inhibit pain or itching without causing a stinging or burning sensation to the patient. However, it is preferable to include other pharmaceutical agents into the anti-hyperalgesic formulations such as antibacterials, antivirals, antifungals, anti-inflammatories and antiseptics which will prevent or eliminate infection and help the healing process.

Antibacterial Agents/Antibiotics

Suitable antibacterial agents include: Aminoglycosides, Amphenicols, Ansamycins, β-Lactams, Carbapenems, Cephalosporins, Cephamycins, Monobactams, Oxacephems, Penicillins, Lincosamides, Macrolides, Amphomycin, Bacitracin, Capreomycin, Colistin, Enduracidin, Enviomycin, Fusafungine, Gramicidin(s), Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin Zinc Bacitracin, Tetracyclines, Cycloserine, Mupirocin, Tuberin, 2,4-Diaminopyrimidines, Nitrofurans, Quinolones, Sulfonamides, Sulfones, Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine, and Zibornol.

Preferred antibacterial agents/antibiotics include: Clindamycin, Erythromycin, Tetracycline, Mupirocin, Bacitracin and Neomycin.

Antifungal Agents

Suitable antifungal agents include: Polyenes, Allylamines, Imidazoles, Triazoles, Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionates, Propionic Acid, Pyrithione, Salidylanilide, Sulbentine, Tenonitrozole, Tolciclate, Tolindate, Tolnaftate, Tricetin, Ujothion, and Undecylenic Acid.

Preferred antifungal agents include: Ketoconazole, Clotrimazole, Ciclopirox olamine, Tolnaftate and Naftifine.

Anti-inflammatory Agents

Suitable Anti-inflammatory agents include: Corticosteroids, Aminoarylcarboxylic Acid Derivatives, Arylacetic Acid Derivatives, Arylbutyric Acid Derivatives, Arylcarboxylic Acids, Arylpropionic Acid Derivatives, Pyrazoles, Pyrazolones, Salicylic Acid and derivatives thereof, Thiazinecarboxamides, E-Acetamidocaproic Acid, S-Adenosylmethionine, 3-Amino-4-hydroxy-butyric Acid, Amixetrine, Bendazac, Bucolome, Carbazones, Difenpiramide, Ditazol, Guaiazulene, Heterocyclid Aminoalkyl Esters of Mycophenolic Acid and derivatives thereof, Nabumetone, Nimesulide, Orgotein, Oxaceprol, Oxazole derivatives, Paranyline, Pifoxime, 2-substituted-4, 6-di-tertiary-butyl-s-hydroxy-1,3-pyrimidines, Proquazone and Tenidap.

Antiseptics

Suitable antiseptics include: Guanidines, Halogens/ Halogen Compounds, Nitrrofurans, Phenols, Quinolines, Boric Acid, Chloroazodin, m-Cresyl Acetate, Cupric Sulfate and Ichthammol.

Antiviral Agents

Suitable antiviral agents include: Purines/Pyrimidinones, Acetylleucine, Monoethanolamine, Acridinamide, Alkylisooxazoles, Amantadine, Amidinomycin, Cuminaldehyde Thiosemicarbzone, Foscarnet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

Dispensing the Compositions

The compositions of the present invention may be dispensed as a liquid from a conventional spray bottle by pumping action by which the bottle is air-pressurized, and the liquid is expelled in a relatively fine spray form.

The preferred way of dispensing the compositions of the present invention is in the form of aerosols. Compositions for administration as aerosols are prepared by dissolving an anti-hyperalgesic compound of formula I in the aqueous solution of up to 15% w/w ethanol, propanol or isopropanol, mixing with a volatile propellant, and placing the mixture in a pressurized container having a metering valve to release the mixture in extra fine droplet size.

The liquefied propellant employed typically is one which has a boiling point below ambient temperature at atmospheric pressure. For use in compositions intended to produce aerosols for medicinal use, the liquefied propellant should be non-toxic. Among the suitable liquefied propellants which can be employed are the lower alkanes containing up to five carbon atoms, such as butane and pentane, or an alkyl chloride, such as methyl, ethyl or propyl chlorides. Further suitable liquefied propellants are the fluorinated and fluorochlorinated alkanes such as are sold under the trademarks "Freon" and "Genetron". Mixtures of the above mentioned propellants can suitably be employed.

Preferred liquefied propellants are chlorine free propellants, for example 134a (tetrafluoroethane) and 227c (heptafluoropropane) which can be used as described above. The aerosol sprays are made by nebulizing the solution containing the anti-hyperalgesic compound, using a variety of known nebulizing techniques. The aerosol system consists of a solution of the anti-hyperalgesic compound, and other therapeutic agents, if desired, in a liquid propellant. Both liquid and vapor phases are present in a pressurized container and when a valve on the container is opened, liquid propellant containing the dissolved anti-hyperalgesic compound, and other therapeutic agents, is released in the form of a fine aerosol mist or aerosol wet spray.

There are a variety of commercially available nebulizers to produce the aerosols of the present invention including small volume nebulizers which can be carried ready for use in first aid requiring circumstances.

Compressor driven nebulizers are also available which incorporate jet technology and use compressed air to generate the aerosol. These devices are commercially available, for example, from: Healthdyne Technologies, Inc.; Omron Healthcare Inc.; Mountain Medical Equipment Inc.; and Hospitak Inc.

Dissolution Studies

Dissolution studies were conducted to ascertain the degree of solubility of the anti-hyperalgesic/anti-pruritic compounds used in the formulation of the present invention.

Various concentrations of the alcohol/water mixtures were prepared. At low concentrations of alcohol, e.g., 1 to 2% w/w, extensive stirring was required to dissolve sufficient amounts of the anti-hyperalgesic compounds. The higher the alcohol content of the alcohol/water mixture, the easier the dissolution of the anti-hyperalgesic compounds. However, the ratio of alcohol/water mixture is limited by the stinging, burning sensation caused by the presence of alcohol in the alcohol/water mixture.

Sensitization Studies of the Alcohol/Water Mixtures

Human volunteers rubbed the inside of both their forearms approximately midway between the wrist and the elbow with 100 grit sandpaper to cause dermal abrasion thereon. The treatment produced a reddened abraded area. The abrading process continued until a mild stinging pain was experienced.

The abraded areas were then treated with various ratios of alcohol/water mixtures by spraying the solutions onto the abraded areas. The sprayings were performed in a "double blind" manner so that the volunteers were unaware of the relative concentrations of the alcohol/water mixture.

Responses were tabulated based on the "lowering" or "increasing" of the stinging, burning sensation caused by the sprays as compared with the stinging, burning sensation caused by the abrading process prior to the application of the sprays.

When the responses were tabulated and the code was broken the alcohol/water mixture which had a ratio of 15% w/w or less alcohol, the remaining percentage being water, was found to be the least stinging and burning. Above the 15/85 percent alcohol/water ratio the mixtures caused increased stinging and burning.

Formulations of the Present Invention

Formulations of the present invention contain from about 0.01% w/w to about 40% w/w, and preferably about 1.0% to about 10% w/w of an anti-hyperalgesic compound of formula I or formula II; of from about 0.0% w/w to about 40% w/w, and preferably of from about 1% w/w to about 10% w/w of an additional active ingredient selected from the group consisting of antibacterials, antivirals, antifungals, anti-inflammatory and anesthetics or mixtures thereof, and of from about 20% w/w to 99.09% w/w of a solvent consisting of from about 1% w/w to about 15% w/w, and preferably of from about 2% w/w/ to about 10% w/w of an alcohol selected from the group consisting of ethanol, propanol and isopropanol or mixtures thereof and of from about 99% w/w to about 85% w/w water.

Illustrative examples follow.

EXAMPLE 6

100 grams of 4-(p-chlorophenyl)-4-hydroxy-N,N-dimethyl-α,α-diphenyl-1-piperidine-butyramide was dissolved in 2 liter of a 5% w/w ethanol/95% w/w water mixture with agitation. The solution was transferred to a pump action spray bottle.

Similarly, using analogous procedures, the following formulations were prepared in which "other active agents" denote one or more of an antibacterial, antifungal, antiviral, antiseptic or anti-inflammatory agent.

EXAMPLES 7-11

| % w/w Anti-hyperalgesic Compound | % Other Active Agent | % Alcohol/Water Solution |
| --- | --- | --- |
| 1 | 0.2 | 1 |
| 1 | 0.0 | 1 |
| 2 | 0.5 | 3 |
| 2 | 0.0 | 3 |
| 10 | 7.0 | 8 |
| 10 | 0.0 | 8 |
| 15 | 3.0 | 15 |
| 15 | 0.0 | 15 |
| 40 | 10.0 | 10 |
| 40 | 0.0 | 10 |

Formulations of the present invention were tested for the inhibition of hyperalgesic activity associated with topical injuries by spraying the formulations from pump-action containers and from pressurized aerosol containers containing a propellant or other gaseous substance. The formulations were found to relieve/inhibit hyperalgesic pain without causing stinging, burning sensation upon application to a topical injured site.

Formulation of the present invention were tested for anti-pruritic activity as described by the following test method.

TESTING FOR ANTI-PRURITIC ACTIVITY

Testing was performed in a mouse scratch model under blind conditions.

Groups of 8-10 male Swiss albino mice (Hilltop Lab Animals, Inc., Scottsdale, Pa.), weighing 2.5-2.6 g, were used in the testing. They were housed under controlled temperature of 23-25° C. Food and water were freely available. Before the experiments, the mice were weighed, put into individual boxes and allowed to acclimate for 30 min.

Materials

Vehicle used to dissolve the test compounds: 20% w/w cremophor EL.

To induce scratching Compound 48/80 (Sigma, St. Louis, U.S.A.) was used which has been shown to produce an itch sensation in humans (Armstrong et al., J. of Physiol., 120: 326, 1953).

The compounds to be tested for anti-pruritic activity were dissolved in the vehicle of 20% w/w cremophor EL.

Method 100 ml of the vehicle (3-5 doses, n=8-10) was injected s.c. into the back of the neck of mice 20 min. before challenging them with 100 μl of Compound 48/80 (2 mg/ml; 50 μg) injected s.c. into the back of the neck. One minute later the mice were observed for 30 min. and the number of hindleg scratching movements directed to the neck was counted.

The vehicle-injected mice scratched 79±16 times in the 30 min after the standard challenge with Compound 48/80.

To each mouse of a group of 8-10 mice previously subjected to the standard challenge various doses of the compounds, to be tested for anti-pruritic activity, were administered s.c. into the back of the neck. One minute later the mice were observed for 30 min and the number of hindleg scratching movements directed to the neck was counted.

For each group of 8-10 mice, the mean values for scratching were normalized to relative % antagonism of scratching and then plotted vs. dose of test compounds. Interval estimates of mean A50 were determined by nonlinear regression analysis (Kalcida Graph) and mean % inhibition of scratching was calculated.

The following compounds were tested:

(1) 1-[4-(4-Hydroxy-4-phenyl-1-piperidino)-2,2-diphenylbutryl]piperidine;

(3) 4-(p-Bromophenyl)-4-hydroxy-N-N-dimethyl-α,α-diphenyl-1-piperidinebutyramide; and (6) 4-(p-Chloropehnyl-4-hydroxy-N-N-dimethyl-α,α-diphenylpiperidine-1-butyramide[loperamide].

Each compound (1, 3, 6) antagonized Compound 48/80-induced scratching in a dose-related manner. Results are shown in Table C.

TABLE C

| | Mean % Inhibition of Scratching | |
|---|---|---|
| Compound | Dose (mg/kg, s.c.) | Mean % Inhibition |
| (1) | 2.5 | 32 |
| | 5.0 | 65 |
| | 10.0 | 83 |
| (2) | 1.0 | 35 |
| | 2.5 | 68 |
| | 5.0 | 94 |
| (3) | 0.5 | 18 |
| | 1.0 | 47 |
| | 2.5 | 65 |

Other compounds tested have shown similar anti-pruritic, dose-responsive activity in the range of from about 15 to about 95% based on doses of form about 0.5 to 10.0 mg/kg, s.c.

It should be understood by those skilled in the art that, while the invention has been described and illustrated above in connection with certain specific embodiments, many variations and modifications may be employed without departing from the scope of the invention.

What is claimed is:

1. A method for the prevention or treatment of pruritus in a patient comprising administering to said patient an effective anti-pruritic amount of a formulation comprising:

(A) a peripheral anti-hyperalgesic compound of the formula (II)

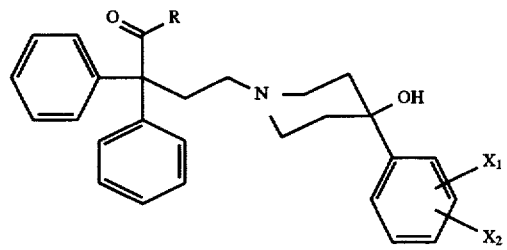

II wherein

R is $N(CH_3)_2$, $N(CH_2CH_3)_2$, $N(CH_3)C_2H_5$, $N(CH_2)_4$, $N(CH_2)_5$ or $N(CH_2CH_2)_2O$; and $X_1$ and $X_2$ are independently H, Cl, Br, F or $CF_3$ and wherein said antihyperalgesic compound has a peripheral selectivity of from about 251 to about 1,280; and (B) a solvent mixture for the compound of formula II comprising: a) up to about 15% w/w of an alcohol selected from the group consisting of ethyl alcohol, propyl alcohol and isopropyl alcohol or mixtures thereof; and b) greater than or equal to 85% w/w water.

2. The method for the prevention or treatment of pruritus in a patient comprising administering to said patient an effective anti-pruritic amount of a formulation according to claim 1 wherein said peripheral anti-hyperalgesic compound is selected from the group consisting of:

1-[4-(4-Hydroxy-4-phenyl-1-piperidino-2,2-diphenylbutyryl]piperidine 4-(p-Chlorophenyl)-4-hydroxy-N-ethyl-N-methyl-α,α-diphenyl-1-piperidinebutyramide 4-(p-Bromophenyl)-4-hydroxy-N,N-dimethyl-α,α-diphenyl-1-piperidinebutyramide 1-{4-[(3,4-Dichlorophenyl)-4-hydroxy-1-piperidino]-2,2-diphenylbutyryl}pyrrolidine 1-{4-[(4-Chlorophenyl)-4-hydroxy-1-piperidino]-2,2-diphenylbutyryl}pyrrolidine 4-(p-Chlorophenyl)-4-hydroxy-N,N-dimethyl-α,α-diphenyl-1-piperidinebutyramide 4-(p-Fluorophenyl)-4-hydroxy-N,N-dimethyl-α,α-diphenyl-1-piperidinebutyramide 4-(4-Chloro-3-trifluoromethyl-phenyl)-4-hydroxy-N,N-dimethyl-α,α-diphenyl-1-piperidinebutyramide 1-[4-(4-Hydroxy-4-phenyl-1-piperidino)-2,2-diphenylbutyryl]pyrrolidine and 1-{4-[4-Hydroxy-4-(3-trifluoromethylphenyl)-1-piperidino-2,2-diphenylbutyryl}morpholine.

* * * * *